US008628481B2

(12) United States Patent
Lang et al.

(10) Patent No.: US 8,628,481 B2
(45) Date of Patent: Jan. 14, 2014

(54) RESPIRATION DETECTING ARRANGEMENT

(75) Inventors: Bernd Lang, Grafelfing (DE); Stefan Schatzl, Weilheim (DE)

(73) Assignee: Map Medizin-Technologie GmbH, Martinsried (DE)

( * ) Notice: Subject to any disclaimer, the term of this patent is extended or adjusted under 35 U.S.C. 154(b) by 124 days.

(21) Appl. No.: 13/112,681

(22) Filed: May 20, 2011

(65) Prior Publication Data

US 2011/0218452 A1 Sep. 8, 2011

Related U.S. Application Data

(63) Continuation of application No. 11/919,496, filed as application No. PCT/EP2006/003754 on Apr. 24, 2006, now Pat. No. 7,967,760.

(30) Foreign Application Priority Data

Apr. 29, 2005 (DE) .......................... 10 2005 020 162

(51) Int. Cl.
*A61B 5/08* (2006.01)
(52) U.S. Cl.
USPC .......................................... 600/534; 600/529
(58) Field of Classification Search
USPC .................................................. 600/529–543
See application file for complete search history.

(56) References Cited

U.S. PATENT DOCUMENTS

| 1,851,579 | A |   | 3/1932 | Hixon |
| 3,268,845 | A | * | 8/1966 | Whitmore ....................... 338/47 |
| 4,602,643 | A |   | 7/1986 | Dietz |
| 4,924,876 | A | * | 5/1990 | Cameron ....................... 600/538 |
| 4,989,612 | A | * | 2/1991 | Fore ............................... 600/534 |
| 5,022,402 | A |   | 6/1991 | Schieberl et al. |

(Continued)

FOREIGN PATENT DOCUMENTS

| EP | 1 374 767 A2 | 1/2004 |
| JP | 03-121051 | 5/1991 |

(Continued)

OTHER PUBLICATIONS

International Search Report for PCT/EP2006/003754 mailed Sep. 6, 2006.

(Continued)

*Primary Examiner* — Navin Natnithithadha
*Assistant Examiner* — Meredith Weare
(74) *Attorney, Agent, or Firm* — Nixon & Vanderhye PC

(57) ABSTRACT

The present application is directed to a detector to detect or generate measuring signals that are indicative of the respiration of a person, wherein said detector can be used advantageously in view of hygiene and stands out due to a simple and robust configuration. According to a first aspect, the detector detects a signal that is indicative of the activity of the respiratory muscles of a person to be examined, the detector comprising a band which, in the application position, is passed around a torso region which widens and narrows when the person to be examined breathes, as well as a structure that is included in the band and loaded in accordance with the narrowing or widening of the torso region. The structure is configured such that it causes a change in the volume of a measuring space device depending on a tensile force. It is thus advantageously possible to detect or measure the forces acting on the band in a non-electric manner and, on the basis of this detection or measurement, draw conclusions relating to the widening or narrowing of the torso.

16 Claims, 4 Drawing Sheets

(56) References Cited

U.S. PATENT DOCUMENTS

Figure 1:
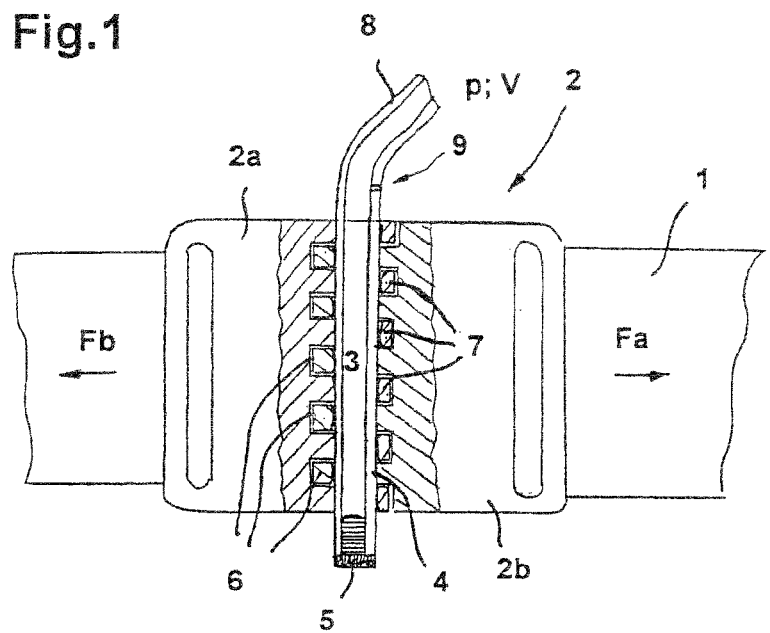

| | | | |
|---|---|---|---|
| 5,074,299 A | 12/1991 | Dietz | |
| 5,088,501 A * | 2/1992 | Niewisch | 600/534 |
| 5,191,893 A * | 3/1993 | Reiten | 600/534 |
| 5,611,349 A * | 3/1997 | Halleck et al. | 600/534 |
| 5,727,562 A * | 3/1998 | Beck | 600/534 |
| 5,864,291 A | 1/1999 | Walton | |
| 6,461,307 B1 * | 10/2002 | Kristbjarnarson et al. | 600/534 |
| 7,967,760 B2 * | 6/2011 | Lang et al. | 600/534 |
| 2001/0007923 A1 | 7/2001 | Yamamoto | |
| 2009/0024048 A1 | 1/2009 | Lang et al. | |

FOREIGN PATENT DOCUMENTS

| | | |
|---|---|---|
| JP | 08-509405 | 10/1996 |
| JP | 2001-190526 | 7/2001 |
| JP | 2005-074012 | 3/2005 |
| WO | WO 02/069878 | 9/2002 |

OTHER PUBLICATIONS

Office Action issued on May 8, 2012 in corresponding Japanese Application No. 2008-508130 (with translation).

Office Action dated Mar. 28, 2013 issued in corresponding European Application No. 11151951.8.

Office Action issued in Australian Patent Application No. 2013200497 issued on Sep. 26, 2013.

Office Action issued in Japanese Patnet Application No. 2012-000825, issued on Oct. 22, 2013 (with translation).

* cited by examiner

RESPIRATION DETECTING ARRANGEMENT

This application is a Continuation of application Ser. No. 11/919,496 filed Oct. 29, 2007, which is a National Phase of International Application No. PCT/EP2006/003754 filed Apr. 24, 2006, which claims foreign priority to German Application No. 102005020162.8 filed Apr. 29, 2005, the entire contents of each of which are hereby incorporated by reference.

The present invention is directed to a detecting means for detecting or generating measuring signals that are indicative of the respiration of a person.

It is the object of the present invention to provide a detecting means for detecting or generating signals that are indicative of the respiration of a person, wherein said detecting means can be used advantageously in view of hygiene and stands out due to a simple and robust configuration.

According to a first aspect of the present invention, this object is achieved by a detecting means for detecting a signal that is indicative of the activity of the respiratory muscles of a person to be examined, said means comprising a band means which, in the application position, is passed around a torso region which widens and narrows in response to the respiration of the person to be examined, as well as a structure that is included in the band means and loaded in accordance with the narrowing or widening of the torso region, wherein said structure is configured such that it causes a change in the volume of a measuring space means depending on a tensile force.

It is thus advantageously possible to detect or measure the forces acting on the band means in a non-electric manner and, on the basis of this detection or measurement, draw conclusions relating to the widening or narrowing of the torso.

In accordance with a particularly preferable embodiment of the present invention, the structure is configured as a buckle means. Said buckle means can be realized like a belt buckle and comprise bracket portions through which the respective end portions of the band means are passed. The buckle means can comprise adjusting means, e.g., clamping means or adjusting eyelets which allow a respective fixing, in particular clamping of the end portions of the band means.

In accordance with a particularly preferable embodiment of the present invention, the detecting means is configured such that the change in the volume of the measuring space means is caused by squeezing or compressing an elastically deformable chamber means. Particularly advantageously, said chamber means can be realized by a tube portion.

It is possible to pass the tube portion in such a manner through the buckle means that the tube portion is squeezed in accordance with the respiration-synchronously changing tensile loading of the belt means. In response to said squeezing, the interior of the tube portion is changed. The resulting displacement of the air in the tube portion can be detected by means of pressure measuring means or small volume flow sensors and used for generating the signals that are indicative of the tensile loading.

In accordance with a particularly preferable embodiment of the present invention, the buckle means is divided in two segments. These two segments can be configured such that they alternatingly surround the tube portion and squeeze it under the influence of respective tensile forces acting on the individual segments.

It is possible to configure the walls which alternatingly surround the tube portion in such a manner with respect to their geometry that a favorable squeezing or relaxation of the tube portion is obtained under the influence of said tensile forces.

The change in the volume which is caused by loading the measuring space means in accordance with the present invention can advantageously be transferred via a measuring tube arrangement to a measuring means. In the area of this measuring means there is preferably a pressure-sensitive structure which converts the respiration-synchronously changing pressure in the measuring tube into suitable analog or digital signals.

Said measuring means can be configured such that a plurality of measuring tube means can be coupled thereto for realizing a corresponding multi-channel recording.

The above detecting means for detecting respiration-synchronously changing tensile forces in a belt system being passed around the torso region of the person to be examined can be configured such that particularly relevant respiration-motor or respiration-mechanic properties can be detected in an advantageous manner.

The present invention is further directed to a measuring arrangement which comprises a detecting means of the kind described above, wherein said measuring arrangement further comprises a measuring tube and a measuring means which is coupled via said measuring tube with the detecting means for recording the tensile force detection of the band means caused by the detecting means.

This measuring arrangement allows a potential-free signal measurement from the patient, thereby avoiding electrically conducting structures.

This measuring means is advantageously configured such that its signal recording capacity extends over a pressure signal range including also any pressure signals measured by nasal cannula means.

The measuring arrangement can comprise a storage medium, in particular an exchangeable storage medium, e.g., in the form of a memory card or in particular a USB flash stick. The measuring means preferably further comprises a receiving means for receiving a battery means for operating the measuring means independent from the network and/or in a wireless manner. The measuring means can be configured as an ambulant, compact module or recording means which can be carried by the patient and comprises a housing means having a flat configuration.

The detecting means of the present invention cannot only be used for diagnosing the respiratory behavior in a user, but it can also be integrated in a respiratory system if required, wherein the measuring signals generated by the detecting means can be taken into consideration in the further control of the respiratory gas supply. The detecting means of the present invention is particularly suitable for detecting the sleep respiration of a person to be examined. However, the field of application of said detecting means is not limited to the medical field. In particular, it can also be used in different applications for monitoring the respiratory motoricity, in particular for optimizing respiration.

The band means can be configured as a disposable band means so that for each patient to be examined a new band means can be used and coupled to the buckle means. It is also possible to provide a tube-like disposable attachment or other hygiene cover, e.g., from a hygiene paper, by means of which the above detecting means or at least its band and buckle means can be covered. It is possible to configure the detecting means, in particular the buckle means, the band means and optionally also the measuring tube as a disposable unit which can be disposed of after the measurement.

It is possible to provide spring-type or other calibration possibilities which guarantee, on the one hand, a sufficient pre-stressing of the belt placed around the patient and, on the other hand, a sufficient ability to widen the thus formed loop. It is possible to realize the band material intended for forming the belt in a relatively tension-proof manner and to generate the required flexibility by structures, e.g., spring or rubber mechanisms, provided in the region of the buckle means. However, it proves to be particularly advantageous to select the band material such that it has a sufficient elasticity and the buckle means essentially only functions as a force measuring means.

Figure 2:
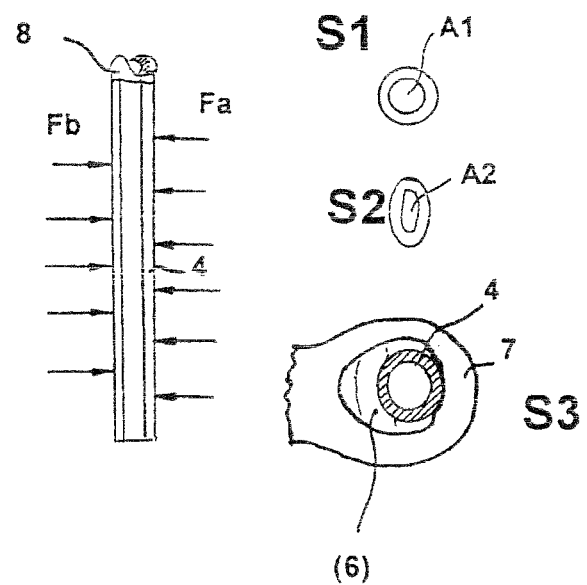
Figure 3:
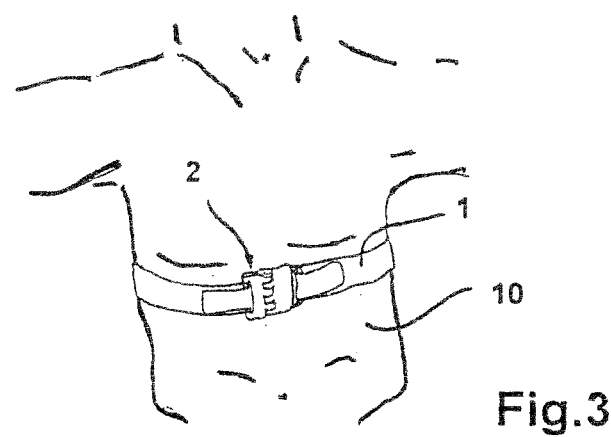
Figure 4:
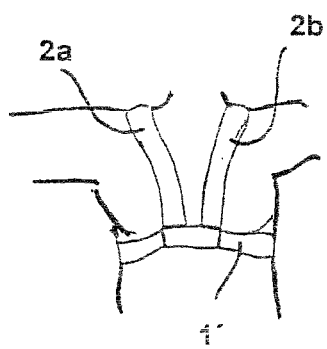
Figure 5:
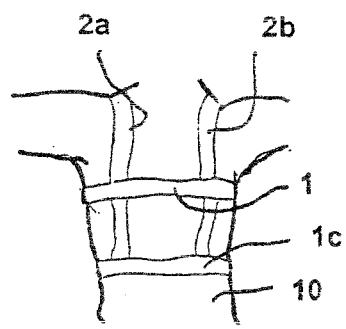
Figure 6:
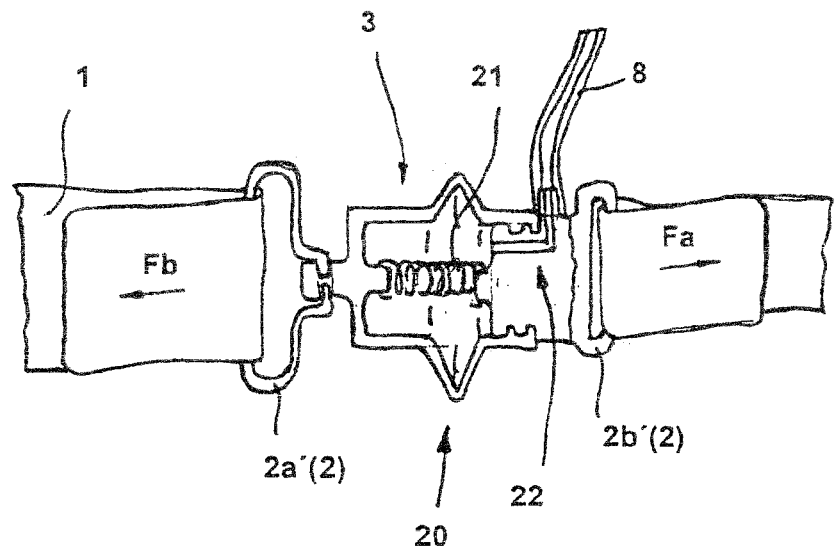
Figure 7:
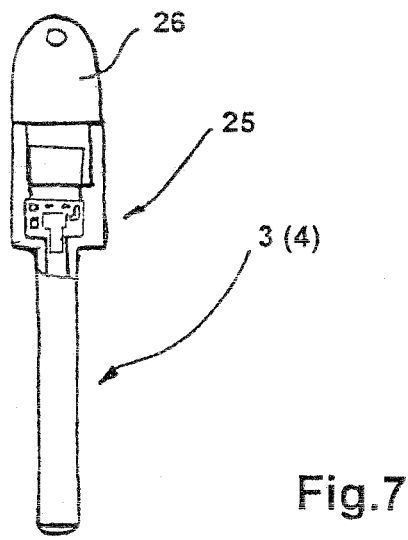
Figure 8:
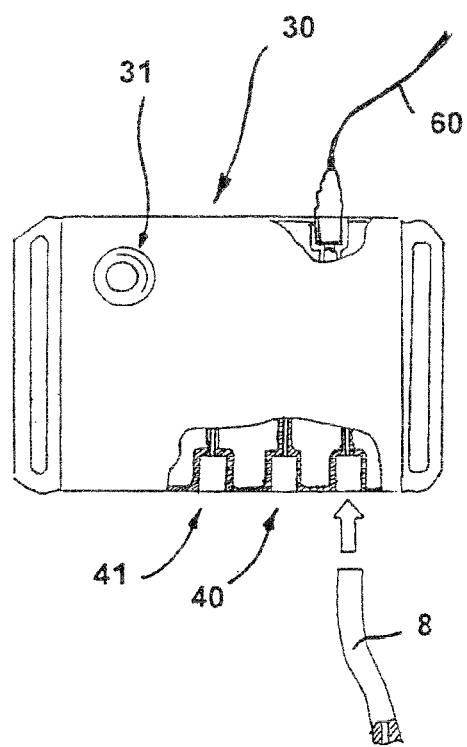

Further details and features of the present invention can be taken from the following description in combination with the drawings in which FIG. 1 is a principle view for explaining the structure of a preferred variant of the detecting means of the present invention, FIG. 2 is a sketch for explaining the load and the resulting change in the volume of a tube portion, FIG. 3 is a torso sketch showing the application of a detecting means of the present invention, FIG. 4 is a further torso sketch illustrating a further way of guiding the band, optionally for a plurality of measuring channels, for an extended examination of the respiratory activity, FIG. 5 is a further torso sketch further illustrating a further way of guiding the band for detecting the respiratory activity, FIG. 6 is a simplified illustration for explaining a further variant of a measuring transducer of the present invention, FIG. 7 is a sketch for explaining a plug-in sensor variant of the detecting means of the present invention, FIG. 8 is a simplified illustration for explaining the structure of a measuring means for converting the recording of the respiration-synchronously alternating pressure signals generated by means of the detecting means of the present invention.

The detecting means shown in FIG. 1 serves for detecting a signal that is indicative of the activity of the respiratory muscles of a person to be examined. Said detecting means comprises a band means 1 which—in the application position (cf. FIG. 3)—is passed around a torso region which widens upon inspiration of the person to be examined and narrows accordingly upon expiration. The band means includes a structure being configured as a buckle means 2 and being loaded upon widening of the torso region by the tensile forces Fa, Fb accordingly acting in the band means 1. Said structure is configured such that it causes a change in the volume of a measuring space means 3.

In the shown embodiment the structure is a buckle means 2, as already mentioned. The change in the volume of the measuring space means 3 is caused by squeezing elastically deformable walls of the measuring space means 3. In the shown embodiment, the elastically deformable walls form an elastic chamber means which as such is realized by a tube portion 4. The ends of the tube portion 4 are closed by an insert 5. The tube portion 4 is surrounded by eyelet portions 6, 7 alternatingly belonging to a left segment 2a and a right segment 2b.

The shown mechanism allows a squeezing of the tube portion 4 in accordance with the tensile forces Fa, Fb acting on the belt means 1. By squeezing the tube portions 4, the volume of the measuring space means 3 formed by the tube portion 4 changes. Due to the change in the volume, the included air is displaced, in particular moved out. This air displacement can be detected in particular if the measuring tube 8 is closed to a large extent by a measuring means which will be explained in detail below. It is possible to provide a bypass throttle bore 9 in the measuring tube 8 or in particular in the plug or connector 5 or also in the region of the measuring means: By means of this throttle bore it is possible to realize a high-pass filter which guarantees that the average pressure in the measuring tube means 8 corresponds for a long time to the ambient pressure and no deviation takes place.

FIG. 2 is a sketch showing how the tube portion 4 of the measuring tube 8 is loaded by the forces FA, FB coupled in via the segments 2a, 2b. Due to the shown loads, the tube portion 4 of the measuring tube 8 deforms from the initial state having an inner cross-section A1 as shown in sketch S1 into the squeezed deformed state shown in sketch S2. In this deformed state the tube portion 4 has an inner cross-section A2 being smaller than the inner cross-section A1 shown in sketch S1.

It is possible to configure the eyelets or squeezing structures surrounding the tube portion 4 in such a manner as regards their geometry that they favor or at least do not considerably hinder the deformation of the tube portion 4. To this end, the eyelet portions preferably have an opening cross-section which is larger than the outer cross-section of the measuring tube portion 4.

As shown in FIG. 3, the detecting means of the present invention is particularly suitable for detecting the widening and narrowing of the torso 10 of a person to be examined. The band means 1 is passed around the torso 10. The band means 1 includes the structure which, in the present case, is configured as a buckle means 2. The tensile forces acting on the band means 1 as the torso 10 widens are detected by the squeezing of a measuring space means 3 caused by the buckle means 2 (cf. FIG. 1).

FIG. 4 shows a further way of guiding the band. On the basis of the tensile force measuring principle of the detecting means of the present invention it is possible to realize a multi-channel measuring system by means of which respiration-motor properties of the respiration of the patent to be examined can be recorded in a multi-channel manner. For example, it is possible to detect, in addition to an elongation of the lower band means 1', also an elongation or widening of the upper band means 2a, 2b shown in FIG. 4.

FIG. 5 shows a further way of guiding the band. In accordance with this variant it is possible to detect, in addition to a widening of the upper portion of the torso 10 by the upper band means 1', also movements of the respiration muscles in the area of the diaphragm by means of a band means 1c that is arranged further below and extends over the lower lung area. In this variant, too, it is possible to additionally record tensile forces in the band regions 2a and 2b in a multi-channel manner by accordingly coupling them in a detecting means of the present invention.

FIG. 6 shows a further variant of a pneumatic measuring transducer of the present invention in this variant, the respiration-synchronously alternating tensile forces Fa, Fb prevailing in the band means 1 cause a change in the volume of the measuring space means 3. In this embodiment, too, the measuring space means 3 is included in a bracket means 2 comprising left and right bracket portions 2a', 2b'. In this embodiment, the measuring space means is also configured as an elastically deformable structure and comprises a portion which can be accordingly widened in response to the tensile forces acting on the band means 1. In this embodiment, this portion is realized as a corrugated sheathing portion 20. A spring means 21, by means of which a specific pre-loading of the detecting means is achieved, is embedded in the corrugated sheathing portion 20. It is possible to realize said spring means 21 as part of a calibration system. Via a measuring tube means 8, the change in the pressure and/or volume in the area of the measuring space means 3 can be detected via corresponding connection channels 22 and supplied to a corresponding measuring means. Different from the squeezing variant, in this mechanism the measuring chamber volume is increased as the band widens (inspiration) and thus a measuring signal is obtained which is reversed relative to the measuring signal of the squeezing variant.

FIG. 7 shows a variant of the measuring space means 3 which as such comprises an elastically deformable tube portion 4, similar to the above description relating to FIG. 1. Deformation of this tube portion 4 directly leads to pressure changes in the interior of the measuring space means 3. Said pressure changes can be detected by a miniaturized measuring transducer means 25 and transmitted to a detachably coupled storage means 26, in the present case a USB flash stick. The shown means can comprise an energy storage means, e.g., in the form of a button cell battery. It is also possible to realize the measuring transducer circuit such that the energy required for generating and recording signals is provided directly by the pressure sensor.

FIG. 8 shows a measuring means provided for converting and recording signals generated by means of the detecting means described above. Said measuring means 30 is configured as a multi-channel measuring means. An end portion of the measuring tube 8 can be coupled (e.g. inserted into a receiving bore or put on a measuring connection) to said measuring means 30. The pressure changes coupled in the measuring tube 8 during the respiration-synchronous squeezing of the tube portion 4 (cf. FIG. 1) can be recorded by the shown measuring means and preferably stored in digital form.

The measuring means 30 is configured such that it can be activated by a switch means 31. The pressure fluctuations passed by the measuring tube 8 to the measuring means 30 can be recorded in accordance with different recording concepts which are preferably stored in the measuring means 30 in a program-based manner. Recording can preferably take place in such a manner that the course of the individual breaths of the person to be examined can be determined with a relatively high resolution (high-resolution raw data recording). It is possible to use the shown measuring means 30 in addition to the conventional recording of the respiration of the patient for diagnosis purposes also for further controlling the respiration of the patient by pressure.

It is possible to configure the measuring means 30 such that it is also possible to record signals that are indicative of the nasal or oral respiratory gas flow of a person to be examined. In the shown variant, the measuring means 30 comprises further connection portions 40, 41 via which also pressure signals can be coupled for the purpose of further recording which can be measured, e.g., by a nasal cannula means or other detecting means for detecting the respiratory gas flow from the patient to be examined.

In accordance with a further aspect of the present invention, the detecting means also comprises a measuring channel for generating a recording signal that is indicative of the oxygen saturation of the blood. To this end, the detecting means 30 can be configured such that it can be connected to a light guide means 60 for introducing light measured at the patient, e.g., in the area of the nose wings or the extremities, in particular fingers. The light guide can have a plurality of conductors so that the light directed to the patient for the purpose of examination can be generated in the area of the measuring means and guided to the patient via the additional light guide, if required. The reflected light measured at the patient can be returned via the second light guide. Tissue portions with good blood supply, in particular finger tips, the area surrounding the ear and nasal areas, are particularly suitable as measuring positions. The light guides can be attached to these portions by means of suitable application structures. It is possible to provide the light guides with a relatively small coupling head which can otherwise be fixed to the patient by means of an adhesive tape or any other adhesive bandage material.

In the shown measuring means it is possible to measure numerous polysomnogaraphic measuring parameters of a patient in a completely non-electric manner and without use of electrically conductive structures. It is possible to integrate the light guide means 60 in the measuring tube 8 and/or manufacture the measuring tube 8 from a material which is directly suitable as a light guide. The measuring means can also comprise further recording systems and channels, in particular for ECG, EEG or other body-electric potential signals.

What is claimed is:

1. A detecting arrangement for detecting a signal that is indicative of activity of the respiratory muscles of a person to be examined, the detecting arrangement comprising:
    a band that is configured to be passed around a torso region that widens and narrows in response to the respiration of the person to be examined;
    a structure that is included in the band and that is loaded by the band in accordance with the narrowing and widening of the torso region; and
    a measuring space device including a bypass throttle bore, wherein the structure comprises a buckle that is configured such that the buckle squeezes the measuring space to cause a decrease in the volume of the measuring space device when the person inhales.

2. The detecting arrangement according to claim 1, wherein the measuring space device comprises an elastically deformable chamber.

3. The detecting arrangement according to claim 2, wherein the elastic chamber includes a tube portion.

4. The detecting arrangement according to claim 3, wherein the bypass throttle bore is in the tube portion.

5. The detecting arrangement according to claim 4, wherein the tube portion is squeezed by the buckle in accordance with tensile loading of the band.

6. The detecting arrangement according to claim 4, wherein the buckle is divided into two segments, and the two segments surround the tube portion for squeezing it depending on the tensile force.

7. The detecting arrangement according to claim 4, wherein walls surrounding the tube portion have a geometry such that deformation conditions are obtained depending on the tensile force created by squeezing of the tube portion.

8. The detecting arrangement according to claim 1, wherein the detecting arrangement forms part of a multi-channel measuring system.

9. The detecting arrangement according to claim 1, wherein a change in the volume depending on the tensile force applied to the band is passed on to a measuring device via a measuring tube arrangement.

10. The detecting arrangement according to claim 9, wherein the bypass throttle bore is proximate to the measuring device.

11. The detecting arrangement according to claim 9, wherein the measuring device comprises a signal recorder.

12. The detecting arrangement according to claim 9, wherein the bypass throttle bore is configured to maintain a substantially constant average pressure in the measuring tube arrangement.

13. A measuring arrangement comprising a detecting arrangement according to claim 1, the measuring arrangement further comprising a measuring tube and a measuring device coupled to the detecting arrangement via the measuring tube for recording tensile force measuring signals measured by the detecting arrangement.

14. The measuring arrangement according to claim 13, wherein the measuring device is configured such that a signal recording capacity thereof extends over a pressure signal range that also comprises the dynamic pressure signals that can be measured via a nasal cannula detecting the respiratory gas flow from the patient.

15. The detecting arrangement according to claim 1, wherein the structure at least partially surrounds the measuring space device.

16. The detecting arrangement according to claim 1, wherein the bypass throttle bore is located adjacent to the structure.

\* \* \* \* \*